United States Patent [19]
Oota

[11] 4,212,744
[45] Jul. 15, 1980

[54] HAEMODIALYZER APPARATUS

[75] Inventor: Kazuhiro Oota, Nagoya, Japan

[73] Assignee: Asahi Medical Co., Ltd., Tokyo, Japan

[21] Appl. No.: 915,354

[22] Filed: Jun. 14, 1978

[30] Foreign Application Priority Data

Jun. 21, 1977 [JP] Japan .................... 52-73673

[51] Int. Cl.² .................................... B01D 31/00
[52] U.S. Cl. .......................... 210/321 B; 210/323 T
[58] Field of Search ............... 210/253, 295, 321 R, 210/321 A, 321 B, 321 UT, 340, 345, 433 M, 257 M, DIG. 23, 323 T; 128/DIG. 3

[56] References Cited

U.S. PATENT DOCUMENTS

| | | | |
|---|---|---|---|
| 3,579,441 | 5/1971 | Brown | 210/321 B |
| 3,654,148 | 4/1972 | Bradley | 210/257 M |
| 3,734,851 | 5/1973 | Matsumura | 210/DIG. 23 |
| 3,846,295 | 11/1974 | Gibbs | 210/257 M |
| 3,926,797 | 12/1975 | Giqou et al. | 210/22 |
| 4,000,065 | 12/1976 | Ladha et al. | 210/23 H |
| 4,024,059 | 5/1977 | Sausse | 210/195 R |
| 4,075,100 | 2/1978 | Furuta et al. | 210/266 |
| 4,105,556 | 8/1978 | D'Amaddio et al. | 210/152 |

OTHER PUBLICATIONS

"Clinical Performance Characteristics of a New Combined System . . .", Chang et al., Trans. Amer. Soc. Artif. Int. Organs, vol. 21, 1975, p. 502.
DePalma et al., "A New Compact Automatic Home Hemodialysis System", Trans. Am. Soc. Art. Int. Org., vol. 14, 1968.
McCaughan, J. S., "A Combined Dialysis–ion Exchange Resin Unit", Surgery, 10/1964, vol. 56, #4, pp. 750-756.

Primary Examiner—Charles N. Hart
Assistant Examiner—David Sadowski
Attorney, Agent, or Firm—Armstrong, Nikaido, Marmelstein & Kubovcik

[57] ABSTRACT

A haemodialyzer apparatus in which there are disposed two different types of membranes, namely, semi-permeable membranes that are substantially incapable of passing therethrough blood plasma proteins and filter membranes that are capable of passing therethrough blood plasma proteins. By the use of the present haemodialyzer apparatus, in addition to urea, creatinine and the like, the relatively high molecular weight substances such as the peptides having a molecular weight of more than 1,000 as well as the plasma proteins with their functions lowered, which relatively high molecular weight substances cannot be removed by any of the conventional haemodialyzers, can be effectively removed, to a desired extent, from the blood, thereby not only purifying or detoxifying the blood or components thereof but also recovering the toxic substances-absorbing abilities of the plasma proteins so that the patients suffering from renal and/or liver failure may be remedied more satisfactorily.

3 Claims, 12 Drawing Figures

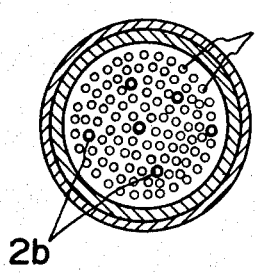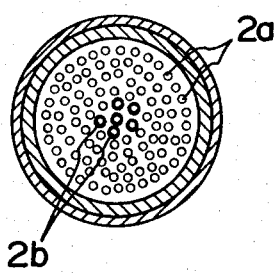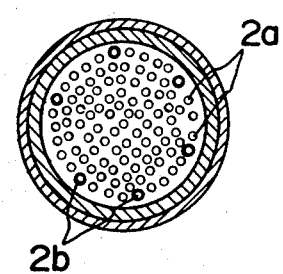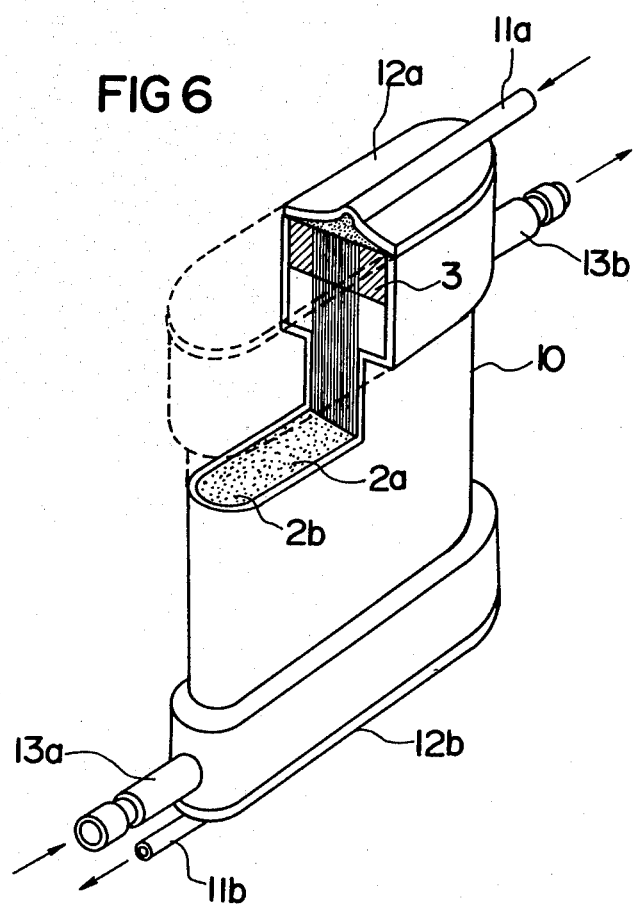

HAEMODIALYZER APPARATUS

The present invention relates to a haemodialyzer apparatus, and more particularly to a haemodialyzer capable of effectively removing relatively high molecular weight substances such as blood plasma proteins with their functions lowered and peptides as well as low molecular weight substances such as urea and creatinine from blood through dialysis and filtration. The term "peptides" as used herein is intended to mean those which are generally called middle molecular substances. These peptides, in general, tend to be accumulated in the body of patients suffering from renal failure, and they are hardly removed by the conventional heamodialyzers. The plasma proteins with their functions lowered include, for example, alubumin, $\beta_2$ microglobulin and retinol-binding protein.

Recently, there have been widely employed haemodialyzer apparatus as an artificial kidney for medically treating patients suffering from renal failure to maintain life of the patients. The conventionally proposed haemodialyzers are of a structure that in a housing there are disposed only semi-permeable membranes such as sheet-shaped, tubular or hollow fiber-type membranes made of, for example, regenerated cellulose such as cuprammonium rayon or deacetylated cellulose. In such conventional haemodialyzers, the dialyzate is contacted with the blood through the semi-permeable membrane, whereby urea, uric acid and the like accumulated in the blood of the patient are removed by dialysis to obtain purified blood. The thus purified blood is recycled to the body of the patient. The conventional haemodialyzer apparatus using the above-mentioned regenerated cellulose membrane is effective for removing the low molecular weight substances. With such conventional apparatus, however, it is difficult to remove the relatively high molecular weight substances that are liable to be accumulated in the body of the patients suffering from renal or liver troubles, for example, peptides having a molecular weight of more than 1,000 and the like.

The haemodialyzer apparatus using these semi-permeable membranes functions to remove substances, taking advantage of diffusion caused by the difference in substance concentration between the liquids respectively present on both sides of the membrane, and hence, the low molecular weight substances can be easily removed, but the relatively high molecular weight substances are difficult to sufficiently remove by such conventional kind of apparatus.

Beside the above-mentioned peptides considered as the middle molecular substance, substances such as methyl guanidine, guanidinosuccinic acid, etc. considered as uremic toxins have the tendency to be strongly bonded to or adsorbed on the plasma proteins such as alubumin, $\beta_2$ microglobulin and retinol-binding protein. In the patients suffering from the renal failure, the function of the kidney is lowered, and therefore, these substances cannot be removed from the plasma protein and then out of the body through the ureter, leading to accumulation of a large quantity of such substances as methyl guanidine and guanidinosuccinic acid in the cells of the body. Accordingly, these substances of uremic toxins are also to difficult to remove by the conventional dialyzing process.

Further, it is noted that in the patients suffering from the renal and/or liver failure, the above-mentioned uremic toxins-adsorbing abilities of such blood plasma proteins as albumin, $\beta_2$ microglobulin and retinol-binding protein are drastically lowered as compared with those of healthy people. Therefore, in the medical treatment of the above-mentioned failures, it is required that the abilities of such blood plasma proteins be recovered. Thus, it has been a problem remaining unresolved in the art to remove the peptides having a molecular weight of more than 1,000 and the uremic toxins bonded to plasma proteins and to recover the uremic toxins-adsorbing abilities of the plasma proteins. The functions of the conventional haemodialyzer apparatus employing the regenerated cellulose membranes are not sufficient for resolving such a problem.

There have been developed synthetic membranes which are capable of removing for the relatively low molecular weight peptides having a molecular weight of about 1,000 but are incapable of permeating the relatively high molecular weight peptides and the blood plasma proteins. Such developed synthetic membranes include those made of polyacrylonitrile, polymethyl methacryrate, polycarbonate, polysulfone and the like. There have been employed the haemodialyzer apparatus and the filter type artificial kidney apparatus utilizing the above-mentioned synthetic membranes in order to treat the patients suffering from the renal failure and prolong the lives of the patients. However, though such haemodialyzer apparatus and the filter type artificial kidney apparatus are effective in removing the peptides having a molecular weight of up to about 1,000 than the conventional haemodialyzer apparatus employing the regenerated cellulose, it was difficult, even with such apparatus, to remove the relatively high molecular weight peptides and the uremic toxins bonded to the plasma proteins such as albumin and the like and to recover the abilities of the plasma proteins with their functions or abilities lowered. Accordingly, with respect to remedy of the patients suffering from the renal failure, there have still been difficulties to be overcome.

With a view to developing a haemodialyzer apparatus for effectively treating the patients suffering from the renal failure without the defects inevitably accompanying the conventional haemodialyzer, the present inventors have made extensive and intensive researches. As a result it has been found that when using a haemodialyzer apparatus in which there are disposed two different types of membranes, namely, semi-permeable membranes that are almost or entirely incapable of passing therethrough blood plasma proteins and filter membranes that are capable of passing therethrough blood plasma proteins, blood or components thereof are contacted with a dialyzate through said semi-permeable membranes and said filter membranes, substances of the kinds over the wide range of from the low molecular weight substances such as urea and creatinine to blood plasma proteins with their activities lowered as well as the relatively high molecular weight peptides having a molecular weight of more than 1,000 can be removed, to a desired extent, from the blood, thereby not only purifying or detoxifying the blood or components thereof but also recovering the toxic substances-adsorbing abilities of the plasma proteins so that the patients suffering from renal failure may be remedied more satisfactorily. Based on such novel finding, the present invention has been made.

Accordingly, it is an object of the present invention to provide a new and improved haemodialyzer apparatus which is extremely effective for treating the patients suffering from renal and/or liver failure as compared with any of the conventional haemodialyzer apparatus.

It is another object of the present invention to provide a haemodialyzer apparatus of the character described above, which is simple in structure and can be easily operated.

The foregoing and other objects, features and advantages of the present invention will be apparent to those skilled in the art from the following detailed description taken in connection with the accompanying drawings in which:

FIG. 3 shows a cross-section taken along the line III—III of FIG. 1;

FIG. 4 and 5 are views which are similar to FIG. 3 and explain varied manners of disposition of the two different types of hollow fiber-shaped membranes;

FIG. 6 is a partly cut-away perspective view of another form of haemodialyzer apparatus using hollow fiber membranes, with illustration of the internal structure of the apparatus;

Figures 1, 2:
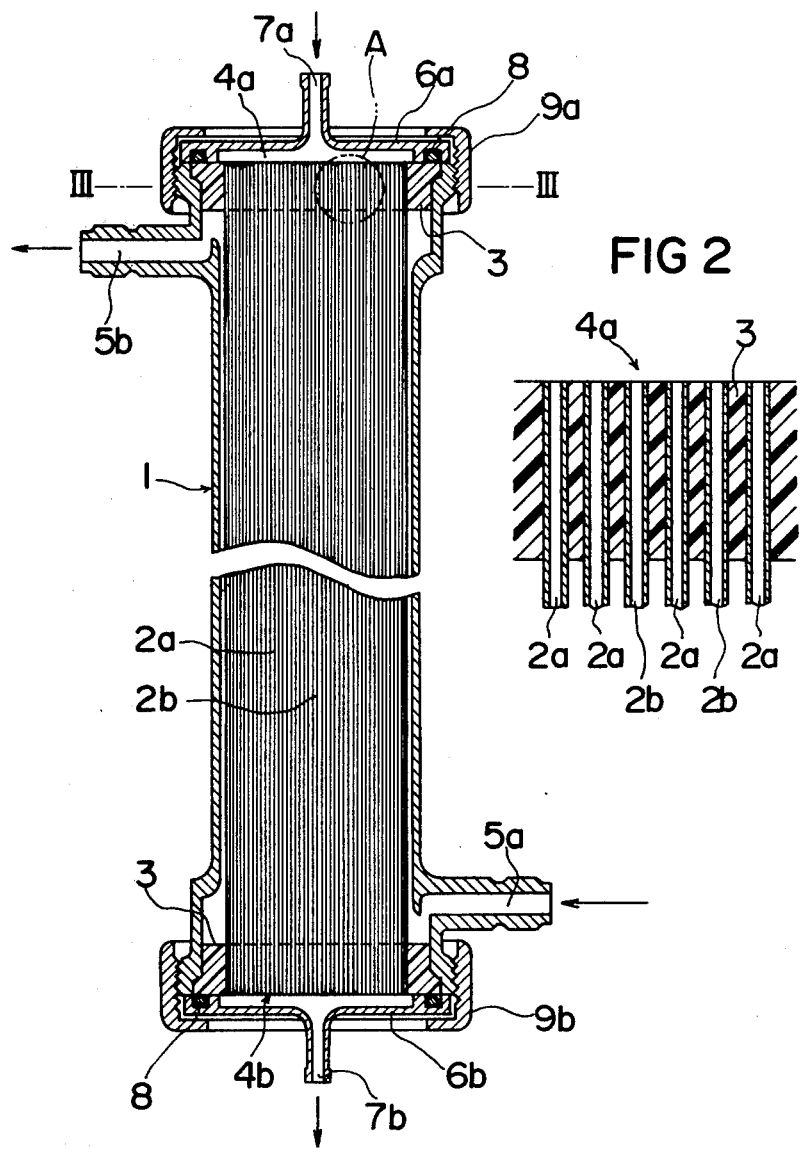
FIG. 1 is a vertical sectional view of one form of haemodialyzer apparatus using hollow fiber membanes according to the present invention.
FIG. 2 is an enlarged view illustrating a portion designated by character A in FIG. 1.

According to the present invention, there is provided a haemodialyzer apparatus which comprises a housing and a plurality of membranes accomodated therein and disposed with respective spacings therebetween to provide alternate passages for blood and a dialyzate, said housing having at least one inlet and one outlet for the blood and at least one inlet and one outlet for the dialyzate, characterized in that said plurality of membranes comprise, in combination, semi-permeable membranes that are substantially incapable of passing therethrough blood plasma preteins and filter membranes that are capable of passing therethrough blood plasma proteins.

As described before, the haemodialyzer apparatus of the present invention is extremely effective for removing from blood not only the low molecular weight substances such as urea and creatinine but also blood plasma proteins together with the uremic toxins bonded thereto as well as the relatively high molecular weight peptides having a molecular weight of more than 1,000. By removing from the blood the middle molecular substances such as the peptides having a molecular weight of more than 1,000 and parts of the uremic toxins-contaminated plasma proteins such as albumin, formation of fresh plasma proteins is promoted so that the toxic substances-adsorbing abilities of the plasma proteins are recovered, thus leading to remedy of the patients suffering from uremia etc.

One type membranes to be used in the haemodialyzer apparatus of the present invention, namely, the semi-permeable membranes that are substantially incapable of passing therethrough blood plasma proteins may be any of the semi-permeable membranes generally used in the conventional haemodialyzer apparatus. Examples of these semi-permeable membranes include hollow fibers of cuprammonium rayon (e.g. Bemberg hollow fibers produced by Asahi Kasei Kogyo K. K.-Japan), flat membranes and tubular membranes (e.g. Cuprofan produced by AKZO Co., Netherlands), cellulose type membranes such as deacelylated cellulose hollow fibers (e.g. those produced by CORDIS Dow Co., U.S.A.) and synthetic polymer type membranes such as polyacrylonitrile flat membranes (produced by RHONE POULENC Co., France), polymethyl methacrylate hollow fibers (produced by TORAY INDUSTRIES, INC., Japan), polycarbonate flat membranes (produced by the American Membrane Co., U.S.A.) and collagen membranes (produced by NIHON HIKAKU SHA, Japan) and the like. These semi-permeable membranes can well pass therethrough relatively low molecular weight substances. It is known that they have a number of pores having an average pore diameter of about 10 to 70 Å.

The other type membranes to be used together with the above-mentioned semi-permeable membranes, namely the filter membranes that are capable of passing therethrough blood plasma proteins are made of a material such as cellulose acetate or the like. The filter membranes have a number of pores of having a pore diameter in the range of about 100 to 1,000 Å so that they are capable of passing therethrough plasma protein. The cellulose acetate membrane to be used as the filter membrane in the haemodialyzer apparatus of the present invention can be easily obtained, for example, by the process as disclosed in the Japanese Patent Application Laid-Open Specification No. 51-93786. According to the process, the cellulose acetate polymer is dissolved homogeneously in a mixture of acetone, methanol, calcium chloride and cyclohexanol and the resulting solution is coagulated by extruding the solution into a coagulating bath of methanol and water through an annular extrusion opening. The pore size of the cellulose acetate membrane can be measured by the method in which the membrane is inserted in a bottle and mercury is then added, followed by application of pressure thereto. The pore size can be determined by calculation according to the following formula:

$$\gamma = \frac{2\sigma \cdot \cos\theta}{p} = \frac{75,000}{p}$$

wherein
 δ: Surface tension of mercury, 480 dynes/cm
 θ: Contact angle, 141.3°
 p: Pressure applied, dynes/cm²
 γ: Radius of pore, Å

As an example of the filter membranes to be employed in the present invention, the cellulose acetate membrane is mentioned above. However, the filter membranes are not limited to such cellulose acetate membranes but there may be employed filter membranes made of other materials such as polycarbonate, polyacryronitlile, polysulfone and the like, so far as not only the materials are suitable for the treatment of blood, that is, the materials do not cause hemolysis, coagulum, thrombus, etc. but also the produced membranes have a number of pores having a pore diameter in the range of about 100 to 1,000 Å so that they are capable of passing therethrough plasma proteins. The structure of the membrane is also not limited to a network structure as disclosed in the Japanese Patent Application Laid-Open Specification No. 51-93786, but the membranes of any other structures may be employed so far as they are capable of passing therethrough plasma proteins. For example, there may be employed even such a polycarbonate membrane (produced by General Electric Co., U.S.A.) as have straight pores formed by neutron beam.

Each of the two different types of membranes as mentioned above may be disposed, in the form of a film, tube or hollow fiber, in a Kiil type, a coil type or a hollow fiber type haemodialyzer apparatus. The blood or its components and the dialyzate are flowed in such a manner that the blood or its component such as blood cell or plasma is contacted with one face of each of the membranes while the dialyzate is contacted with the other face of each of the membranes.

The quantity ratio of the two different types of membranes accomodated in the haemodialyzer apparatus may be varied depending on the treatment purpose, but, taking into consideration the amount of proteins to be synthesized in the body by the time when the next dialysis operation is conducted, there may preferably be employed the two different types of membranes in a specific ratio as will be explained later.

In order to determine a suitable quantity ratio of the two different types of membranes, the following experiments were conducted using cellulose acetate hollow fiber membranes prepared by the process as described in Japanese Patent Application Laid-Open Specification No. 51-93786. The cellulose acetate hollow fiber membranes had an inner diameter of 200$\mu$ and a thickness of 30$\mu$, and had a number of pores of 100 to 1,000 Å in pore diameter. The cellulose acetate hollow fiber membranes were employed in combination with the Bemberg hollow fiber membranes mentioned above and having an inner diameter of 200$\mu$ and a thickness of 15$\mu$. The former was employed in quantities of 0.1, 0.5, 1.0, 2.0 and 5.0% based on the latter in terms of membrane area to provide respective combinations of the two different types of membranes. The thus prepared combinations of the membranes are respectively incorporated in housings in such a quantity as provide a total membrane area of 1.1 m$^2$ and constructed to provide five kinds of cylindrical heat exchange type artificial kidneys. Using these five artificial kidneys, haemodialysis experiments were each carried out for 5 hours at a blood flow rate of 200 ml/min, dialyzate flow rate of 500 ml/min and an ultrafiltration pressure of 200 mmHg. These experiments were conducted employing the same patient suffering from renal failure and being under the same conditions. As a result, 2.5 g, 4.3 g, 10.5 g, 15.1 g and 20.5 g of the plasma proteins were removed respectively in the cases of the filter membrane area rates of 0.1, 0.5, 1.0, 2.0, and 5.0% and 380 mg, 520 mg, 860 mg, 1,250 mg and 1,830 mg of the peptides having a molecular weight of 2,000 were removed respectively in the cases of the filter membrane area rates as mentioned above. On the other hand, when a five-hour haemodialysis experiment for the same patient as mentioned above was carried out under the same conditions by the use of a cylindrical heat-exchanger type haemodialyzer employing therein only the same Bemberg hollow fiber membranes as mentioned above and having a total membrane area of 1.1 m$^2$, the amount of the removed plasma proteins was so extremely small that it was difficult even to trace the amount of the plasma proteins contained in the dialyzate flowing out of the haemodialyzer apparatus. With respect to the peptides also, the amount removed by the five-hour dialysis operation was as small as only 150 mg.

With respect to the problem caused by the removal of plasma proteins, since new plasma proteins are bio-synthesized in the body and can be sufficiently produced, by the time of a next dialysis, more advantageously through administration of essential amino acids and the like to the body, so that the removed plasma proteins can be compensated. In this connection, however, it is noted that in the ordinary patients, the amount of the plasma proteins bio-synthesized for the usually employed period of from a haemodialysis to the next haemodialysis is at most about 20 g. Accordingly, the removal of plasma proteins of more than about 20 g in one-time dialysis operation causes the amount of the plasma proteins in the blood to be decreased below the allowable level. For this reason, it is desired that the filter membrane which can pass plasma proteins be not employed in a quantity more than 5% based on the semi-permiable membrane in terms of membrane area. In the haemodialyzer apparatus according to the present invention, it is generally preferable to employ the filter membrane that is capable of passing therethrough the plasma proteins in a quantity of about 0.1 to 5%, in terms of membrane area, based on the semi-permeable membrane that is substantially incapable of passing therethrough the plasma proteins. The above-mentioned quantity ratio of the two different type membranes which is preferably employable in the present invention applies to the apparatus, irrespective not only of the form of membrane but also of the type of the apparatus. In other words, in any of the apparatus of the Kiil type, coil type, etc. in which there may be employed any of sheet-shaped, tubular and hollow filter-shaped membranes, the same quantity ratio of the two different type membranes may preferably be employed to give the same dialysis performance without any influences of the shape and/or the structure of the apparatus. Furthermore, it is to be noted that the above-mentioned quantity ratio of the two different type membranes may apply to not only the two types of membranes of the materials as mentioned above but also two types of the membranes respectively made of other different materials so far as the different materials respectively provide semi-permeable membranes and filter membranes, the former having a number of pores of 10 to 70 Å in pore diameter and being substantially incapable of passing therethrough plasma proteins, the latter having a number of pores of 100 to 1,000 Å in pore diameter and being capable of passing therethrough plasma proteins.

Referring now to FIG. 1, there is shown one form of haemodialyzer apparatus using hollow fiber membranes according to the present invention. FIGS. 2 and 3 are cross-sectional views of portions of the internal structure of the apparatus, illustrating characteristic features of the present invention. Two different types of hollow fiber membranes 2a and 2b are employed, in combination, in a predetermined proportion in the range as shown below. The two different type hollow fiber membranes are encased in a housing 1 in such a disposition that there is provided alternate passages for blood or its components and a dialyzate. The hollow fiber membrane 2a (semi-permeable membrane made of cuprammonium rayon (having an average pore diameter of 30 Å) and substantially incapable of passing therethrough the plasma proteins. The hollow fiber membrane 2b (filter membrane) is made of cellulose acetate (having a pore diameter of 100 to 1,000 Å) and capable of passing therethrough the plasma proteins. The hollow fiber membranes of the semi-permeable type and the filter type 2a and 2b are mixed at random but in a quantity ratio [(2a/2b)×100] of 0.1 to 5% in terms of membrane area. Both the types of hollow fiber membranes 2a and 2b disposed in parallel are bonded and fixed at their upper and lower ends to a polyurethane resin-made fixation blocks 3. On the fixation blocks 3 are disposed headers 6a and 6b, respectively. The headers 6a and 6b have their respective annular grooves with O-rings 8 fitted thereinto, and pressed by caps 9a and 9b to provide an intake 4a and an exit 4b for the blood or its components. Thus, both the upper and lower ends of the hollow fibers communicate with an inlet 7a and an outlet 7b through the intake 4a and the exit 4b, respectively, as shown in FIG. 1. There is provided an intake 5a for introducing a dialyzate into the housing 1 at its lower portion. An exit 5b for collecting the dialyzate to flow out of the housing 1 opens at an upper portion of the housing 1. In such structure of the haemodialyzer apparatus, the blood or its components (e.g. blood plasma and blood cell and blood platelet) are adapted to contact with the dialyzate through the hollow fiber membranes. Thus, the blood or its components introduced from the inlet 7a flow into the respective insides of both the two types of hollow fiber membranes 2a and 2b via the intake 4a for the blood. The blood flowing through the insides of the respective hollow fibers 2a and 2b contacts with the dialyzate flowing outside the respective two types of hollow fiber membranes 2a, 2b through the membrane walls of the two types of hollow fiber membranes. As a result, not only the low molecular weight substances such as urea, creatinine and the like but also the relatively high molecular substances such as the peptides, plasma proteins and the like are removed at a desired rate that is determined by the doctor. The thus dialyzed blood flows into the exit 4b for the blood, and the purified blood or its components are recycled into the body through the outlet 7b.

In the case of the hollow fiber type haemodialyzer apparatus, there may generally be employed hollow fibers each having an outer diamerter of about 200 to 300μ and a membrane thickness of about 10 to 30μ. As to the number of hollow fibers, there may be employed about 8 to 400 fibers of the filter type 2b with respect to about 8,000 fibers of the semi-permeable type 2a. The hollow fibers 2a and 2b may be arranged at random as illustrated in FIG. 3. Alternatively, as seen in FIG. 4, the hollow fibers of the filter type 2b may be arranged in the central portions of the bundle of hollow fibers. Furthermore, as shown in FIG. 5, the filter type hollow fibers 2b may be disposed in the peripheral portions of the bundle of hollow fibers.

In the arrangement as shown in FIG. 4, the filter membranes 2b which do not serve for substantial dialysis-removal of the low molecular weight substances but serve for removal of the relatively high molecular weight substances even without aid of the dialyzate, are disposed in the central portions of the bundle of hollow fibers in which central portions the dialyzate tends to be prevented from free flowing, while the semi-permeable membranes 2a which are effective for removing the low molecular weight substances are disposed in the peripheral portions in which the dialyzate easily flows. With such arrangement, it is realized to effectively remove not only the low molecular weight substances such as urea and creatinine but also the high molecular weight substances such as the plasma proteins and the peptides. In this connection, however, it should be noted that since the hollow fibers of the filter type 2b are excellent in ultrafiltration characteristics, the blood or its components are more liable to flow to the inside of the hollow fibers 2b rather than to the insides of the semi-permeable type hollow fibers 2a located in the vicinity of the filter type hollow fibers 2b, during the course of the flowing of the blood or its components from the intake 4a to the exit 4b. Accordingly, the flow of the blood or its components in the insides of the hollow fibers 2a located in the vicinity of the filter type hollow fibers 2b is suppressed, thus leading to a difficulty that the blood is liable to undergo coagulation. With a viewpoint of avoidance of such difficulty, the arrangement as shown in FIG. 5 is advantageous. Illustratively stated, when the filter type hollow fibers 2b are disposed in the peripheral portions in which the flow rate of the blood from the intake 4a is relatively low, the coagulation of the blood in the hollow fibers 2a occurring due to the above-mentioned phenomena is effectively prevented.

The haemodialyzer apparatus as shown in FIG. 1 can be easily produced by the following method. That is, the hollow fibers 2a and 2b are encased in a cylindrical housing 1,; a polyurethane resin is applied to the end portions of the cylindrical housing 1 by a centrifugal molding; the surplus portion of urethane resin protruded at both the end portions is cut out by a cutter after the polyurethane has been cured; and the headers 6a, 6b and the caps 8a and 8b are attached to both the end portions.

FIG. 6 shows another embodiment of the present invention employing the hollow fiber membranes of the semi-permeable type 2a and the filter type 2b. The perspective view of FIG. 6 is partly cut-away to show the internal structure. The hollow fibers 2a and 2b are mixed at random and encased in a flat-shape housing 10. The mixed hollow fibers 2a and 2b are bonded and secured at their end portions to a fixation block made of a polyurethane resin 3. The thus formed hollow fiber bundle is communicated, at its both ends, with an inlet 11a and 11b for the blood or its components, respectively. The inlet 11a and the outlet 11b are formed respectively in headers 12a and 12b that are attached to both the upper and lower end portions of the housing. In the side wall structure of the flat-shape housing there are provided an inlet 13a for the dialyzate and an outlet 13b for the dialyzate. Similarly to the apparatus of FIG. 1, this embodiment of the present invention employs therein two different types of hollow fibers 2a and 2b in a quantity ratio as defined before and exhibits a satisfactory performance as in the apparatus of FIG. 1.

Figure 7:
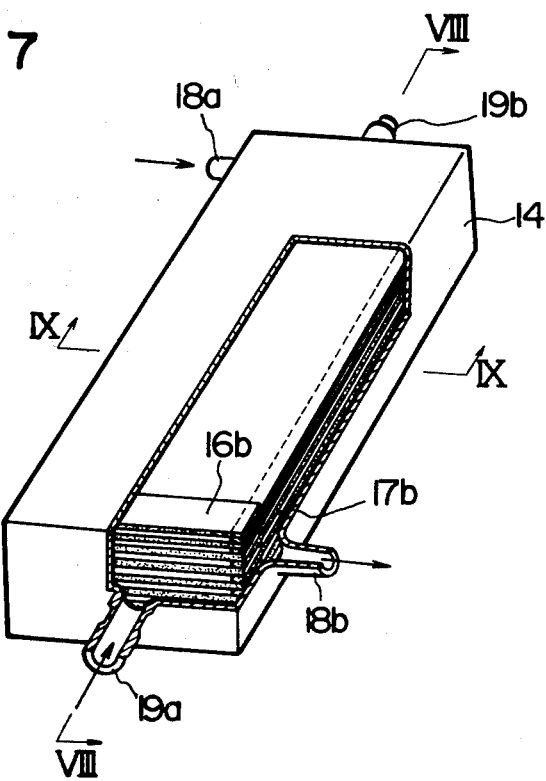
FIG. 7 is a partly cut-away perspective view showing the haemodialyzer apparatus using sheet-shaped membranes according to the present invention.
Figure 8:
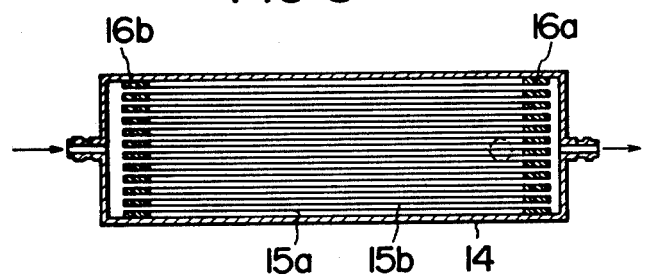
FIG. 8 shows a cross section taken along the line VIII—VIII of FIG. 7.
Figure 9:
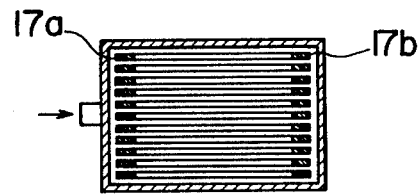
FIG. 9 shows a cross-section taken along the line IX—IX of FIG. 7.

In FIGS. 7 through 9, there is shown a haemodialyzer apparatus using sheet-shaped membranes according to the present invention. In this embodiment, there are employed sheet-shaped membranes 15a made of a cuprammonium rayon that is substantially incapable of passing therethrough the plasma proteins in combination with sheet-shaped membranes 15b made of cellulose acetate capable of passing therethrough the plasma proteins in a quantity ratio (15a/15b) of 100/0.1-5 in terms of membrane area. The membranes 15a and 15b are mixed at random, disposed in a laminate configuration and encased in a rectangular-shape housing 14. The housing is provided with an inlet 18a and an outlet 18b for blood or its components and an inlet 19a and an outlet 19b for a dialyzate. Between the sheet-shaped membranes are liquid-tightly disposed a pair of spacers 16a and 16b and a pair of spacers 17a and 17b in alternate relationship to provide passages for the blood and passages for the dialyzate as clearly seen in FIGS. 8 and 9 so that the blood or its components may be contacted with the dialyzate through the membrane without intermingling therebetween.

Figure 10:
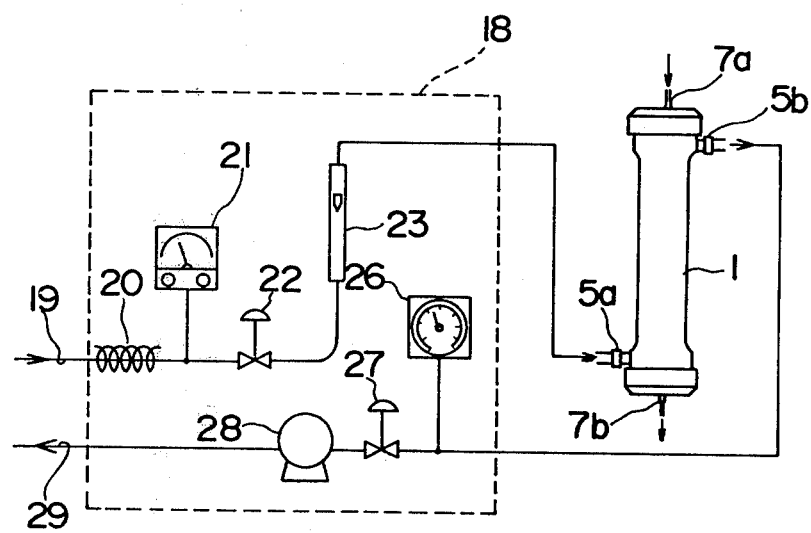
FIG. 10 is a diagrammatic view explaining one mode of actual dialysis by the use of the haemodialyzer apparatus shown in FIG. 1.

FIG. 10 is a diagrammatic view explaining one mode of the haemodialysis which is conducted using the haemodialyzer apparatus shown in FIG. 1. In FIG. 10, numeral 18 designates a bedside monitor. In the monitor 18, upon receiving the flow 19 of the dialyzate fed from a central supplier (not shown), a heater 20 is operated to raise the temperature of the dialyzate to 37° C. while reading the temperature on a thermometer 21. The dialyzate is then flowed to a flow meter 23. While controlling the flow rate of the dialyzate at 500 ml/min. by means of a flow rate adjusting valve 22, the dialyzate is supplied to the heamodialyzer apparatus 1 at the intake 5a for the dialyzate. The dialyzate flows through the dialyzate passages in the haemodialyzer apparatus 1 to contact the blood through the membranes to effect dialysis, so that the urea, the contaminated plasma proteins and the like contained in the blood are removed into the dialyzate. The dialyzate is then flowed out of the apparatus 1 at its dialyzate outlet 5b and again introduced into the bedside monitor 18. The dialyzate introduced in the bedside monitor 18 is sucked by a negative pressure pump 28 and led to a drain pipe 29. At this time, the opening degree of a negative pressure adjusting valve 27 is regulated while reading a negative pressure gauge 26 so that the pressure in the apparatus at its side of the dialyzate is made negative with respect to that of the blood contained in the hollow fibers 2a and 2b.

By the action of the negative pressure, water and the plasma proteins included in the blood are sucked and filtered out of the hollow fibers 2b to the dialyzate side while the low molecular weight substances such as urea and creatinine and the like are dialyzed and removed into the dialyzate out of the hollow fibers 2a. The purified blood or components thereof are returned into the human body from the blood outlet 7b of the apparatus 1.

Figure 11:
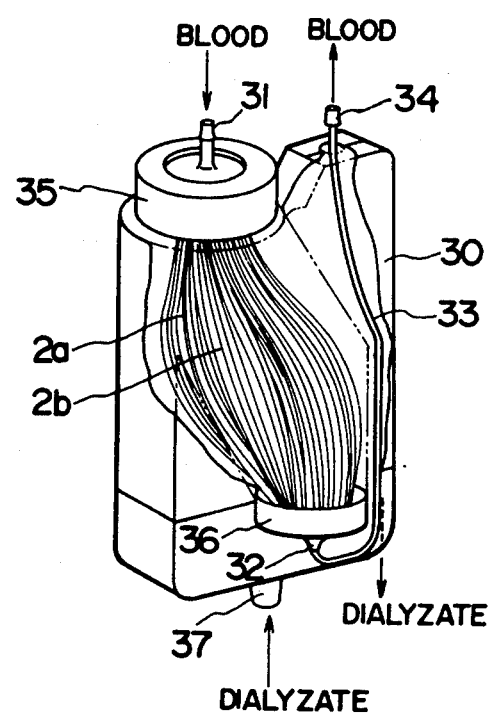
FIG. 11 is a perspective view of still another form of haemodialyzer apparatus, with its casing partly cut-away to illustrate the internal structure.
Figure 12:
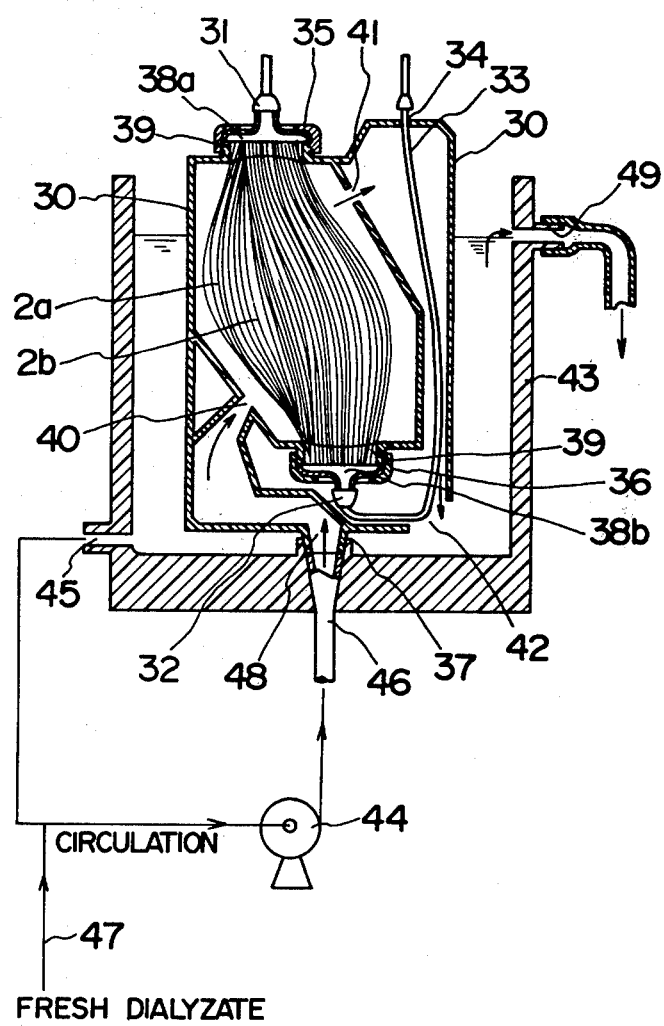
FIG. 12 is a vertical sectional view of a dialyzate-partial recirculation type haemodialyzer system in which the apparatus of FIG. 11 is incorporated.

FIG. 11 is a perspective view of still another form of haemodialyzer apparatus, with its casing partly cutaway to illustrate the internal structure; and FIG. 12 is a vertical sectional view of a partial recirculation type haemodialyzer system in which the apparatus of FIG. 11 is incorporated. The apparatus of FIG. 11 and the system of FIG. 12 are substantially the same as those disclosed in German "Offenlegungschrift" No. 27 16 585, except that the bundle of hollow fibers comprises, in combination, two different types of hollow fiber membranes, namely, semi-permeable hollow fiber membranes 2a that are substantially incapable of passing therethrough the blood plasma proteins and filter hollow fiber membranes 2b that are capable of passing therethrough the blood plasma proteins.

Referring to FIG. 11, the two different types of hollow fibers 2a and 2b are mixed at random and the resulting bundle is encased in a housing provided in a casing 30. The end portions of the hollow fiber bundle are bonded and firmly held by means of a polyurethane resin-made fixation block 39 which is formed by bonding the end portions of the hollow fibers with the polyurethane type adhesives. Both the end portions of the hollow fibers are respectively engaged with headers having an inlet 31 and an outlet 32 for the blood or its components, respectively. The upper and lower headers are respectively pressed by caps 35 and 36 to form an intake portion 38a and an exit portion 38b for the blood or the components thereof. At the lower portion of the casing 30, there are provided an intake 37 and an exit 42 for the dialyzate. The header provided with the outlet 32 for the blood is connected to a conduit 33 and communicates with an upper outlet 34 for the blood. The apparatus of FIG. 11 may advantageously be practically used in the dialyzate-partial recirculation type haemodialyzer system as illustrated in FIG. 12. This apparatus is so constructed as to be accommodated in a tank 43 through engagement of an opening projection 37 provided at the bottom of the casing 30 and communicated with a dialyzate introduction pipe 46. The casing 30 has a dialyzate passage which opens at 48 and communicates with the dialyzate intake 40 of the housing for the bundle of hollow fibers. The conduit 33 connected to the blood outlet 32 is encased in the casing 30 at its mantle portion which is provided outside the housing for the bundle of hollow fibers and led out of the casing 30 through an opening 34. The mantle portion communicates with the inside of the housing through the exit 41 and opens at 42. The tank 43 has a dialyzate drain port 49 at its upper portion for letting the dialyzate overflow and an opening 45 at its lower portion for letting the dialyzate flow out of the tank 43 to be recirculated by a pump 44 while being supplied with fresh dialyzate 47 from a central dialyzate supplier (not shown). In the thus constructed haemodialyzer apparatus; the flow of dialyzate forms a circuit as follows: introduction pipe 46→opening 48→path in casing→intake 40→passage in the housing traversing hollow fibers→exit 41→mantle portion→opening 42→opening 45 (while the dialyzate is partially discharged through drain port 49)→introduction pipe 46. In operation, the blood or its components are caused to pass through the hollow fibers 2a and 2b from the inlet 31 to the outlet 32, and discharged through the conduit 33. In this instance, when the pressure is applied to the blood by, for example, using a pinch cock or the like, removal of the plasma proteins contained in the blood or its components by filtration through the wall membranes of the filter hollow fibers 2b into the dialyzate as well as removal of the low molecular weight substances including urea, creatinine and the like by dialysis through the wall membranes of the semi-permeable hollow fibers 2a into the dialyzate is advantageously promoted.

The present invention may be embodied with various types of modifications or changes in accordance with the technical knowledge of those pertaining to the field without deviating the spirit of and scope of the present invention. It is understood that the haemodialyzer apparatus of the present invention may be applied to the dialysis of the blood or its components e.g. plasma itself to attain high efficiency dialysis.

As described, according to the present invention, there is provided a haemodialyzer apparatus in which there are disposed two different types of membranes, namely, semi-permeable membranes that are substantially incapable of passing therethrough blood plasma proteins and filter membranes that are capable of passing therethrough blood plasma proteins. When using such a haemodialyzer apparatus, blood or componets thereof are contacted with a dialyzate through said semi-permeable membranes and said filter membranes, substances of the kinds over the wide range of from the low molecular weight substances to the relatively high molecular weight substances can be removed from the blood. Particularly, it is to be noted that, by the use of the present haemodialyzer apparatus, in addition to urea, creatinine and the like, the relatively high molecular weight substances such as the peptides having a molecular weight of more than 1,000 as well as the plasma proteins with their functions lowered, which relatively high molecular weight substances cannot be removed by any of the conventional haemodialyzers, can be effectively removed, to a desired extent, from the blood, thereby not only purifying or detoxifying the blood or components thereof but also recovering the toxic substances-absorbing abilities of the plasma proteins so that the patients suffering from renal and/or liver failure may be remedied more satisfactorily.

For demonstrating the excellent effect of the present invention, Application Example is given as follows.

Application Example 9,800 Bemberg hollow fibers (trade name of semi-permeable membrane type cuprammonium rayon hollow fibers produced by Asahi Kasei Kogyo K.K., Japan) that are almost or entirely incapable of passing therethrough the plasma proteins were mixed with 20 filter membrane type cellulose acetate hollow fibers produced by the process as disclosed in Japanese Patent Application Laid-Open Specification No. 51-93786 and capable of passing therethrough the plasma proteins. The above-mentioned semi-permeable type membrane had a membrane thickness of 15$\mu$ and an inner diameter of 215$\mu$. The above-mentioned filter membrane type hollow fibers had a membrane thickness of 30 and an inner diameter of 300$\mu$. The both types of hollow fibers provided a total membrane area of 1.1 m$^2$. Employing the hollow fibers, the apparatus of the structure as shown in FIG. 1 was formed. The apparatus had a capacity of removing 10 to 15 g of the plasma proteins by a five-hour haemodialysis. The haemodialysis was carried out for a 48-year-old male patient suffering from the renal failure and having a body weight of 54 kg using a system as explained referring to FIG. 10. The haemodialysis was conducted three times in a week, and every haemodialysis was effected for 5 hours. The haemodialysis was conducted totally 15 times. Results of the haemodialysis were given in table 1. Before the above-mentioned patient was subjected to the instant haemodialysis by the apparatus according to the present invention, he had been treated by the artificial kidney employing therein deacetylated cellulose type hollow fibers having a total membrane area of 2.5 m$^2$ (manufactured by CORDIS DOW Co., U.S.A.). However, the anaemia of the patient was not cured. After the patient was treated using the present haemodialyzer apparatus, the hematocrit value was considerably increased and the anaemia was cured.

As the index of the binding ability of serum alubumin, there was employed a ratio of HABCA/BCG as will be explained below. The amount of albumin binding with such substances discharged mainly from a liver as BCG (Bromcreson Green $C_{21}H_{14}Br_4O_5S$) and the amount of albumin binding with such substances removed through the kidney as HABCA (4'-hydroxyazobenzenecarboxylic acid, $C_{13}H_{10}O_3N_2$) were determined, and the ratio of HABCA to BCG was used as the index as mentioned above. Such a ratio was taken as to the patient. In case the haemodialysis was conducted using the apparatus of the present invention, the ratio of HABCA to BCG was increased, as compared with the case where the conventional deacetylated cellulose type apparatus was employed, and apparently approximates the value of a normal person, to wit, 0.9 to 0.98. It is clearly understood from the experiment that by subjecting the patient to haemodialysis using the present apparatus the serum albumin with its binding ability lowered disappeared to promote formation of new proteins, thus enabling various symptoms such as anaemia accompanying the renal failure to be cured.

In Table 1, there are shown results obtained just after the dialysis indicated.

Table 1

| Number of dialysis runs, times | | | 3 | 6 | 9 | 12 | 15 |
|---|---|---|---|---|---|---|---|
| Apparatus | | C-D M-5 (Artificial kidney of CORDIS DOW, U.S.A.) | Present invention | — | — | — | — |
| Dialysis conditions | flow rate of blood, ml/min | 200 | 200 | 200 | 200 | 200 | 200 |
| | flow rate of dialyzate, ml/min | 500 | 500 | 500 | 500 | 500 | 500 |
| | ultra filtration pressure, mmHg. | 200–300 | 100–200 | 100–200 | 100–200 | 100–200 | 100–200 |
| Results | BUN (before the dialysis/after the treatment), mg/dl | 72.5/26.2 | 105.6/53.9 | 99.0/31.4 | 76.5/33.1 | 81.0/ | 70.5/28.5 |
| | creatine (before the dialysis/after the treatment), mg/dl | 8.9/4.6 | 11.7/6.7 | 10.4/5.1 | 8.3/4.3 | 11.3/5.3 | 9.7/4.1 |
| | Ht, % | 28.4 | 32.7 | 31.2 | 34.1 | 35.8 | 35.2 |
| | RBC, 10,000/mm$^3$ | 302 | 340 | 330 | 363 | 382 | 363 |
| | HABCA/BCG | 0.46 | 0.51 | 0.63 | 0.62 | 0.73 | 0.74 |

What is claimed is:

1. In a haemodialyzer comprising a housing having an inlet and an outlet for blood and an inlet and an outlet for dialyzate, a plurality of membranes positioned in said housing and fixation block means for holding said membranes at their end portions, in a liquid tight connection, in relation to said housing wherein separate liquid passages for said blood and said dialyzate are formed by said plurality of membranes that are separately communicated with said inlet and outlet for blood and with said inlet and outlet for dialyzate, the improvement wherein said membranes comprise a first plurality of semi-permeable dialyzing membrane means substantially incapable of passing blood plasma proteins therethrough, said dialyzing membrane means contacting all components of said blood on one side thereof and contacting said dialyzate on the other side thereof, and a second plurality of filter membrane means for passing blood plasma proteins and for not passing blood corpuscles therethrough, wherein said dialyzing membrane means and said filter membrane means are held in said fixation block means.

2. A haemodialyzer apparatus according to claim 1 wherein said filter membrane means are present in a quantity of about 0.1 to 5% based on said semi-permeable membrane means, in terms of membrane area.

3. A haemodialyzer apparatus according to claim 2, wherein said filter membrane means are made of cellulose acetate.